United States Patent [19]

Goble

[11] Patent Number: 5,152,764
[45] Date of Patent: Oct. 6, 1992

[54] FEMORAL TUNNEL ENTRY DRILL GUIDE

[76] Inventor: E. Marlowe Goble, 850 E. 1200 North, Logan, Utah 84321

[21] Appl. No.: 884,387

[22] Filed: May 18, 1992

[51] Int. Cl.⁵ .............................................. A61F 2/32
[52] U.S. Cl. .......................................... 606/96; 606/98
[58] Field of Search .................... 606/80, 96, 97, 98, 606/86, 75, 104; 411/174, 175; 403/395, 398

[56] References Cited

U.S. PATENT DOCUMENTS

| | | | |
|---|---|---|---|
| 4,159,716 | 7/1979 | Borchers | 606/96 |
| 4,257,411 | 3/1981 | Cho | 606/96 |
| 4,342,309 | 8/1982 | Eftekhar | 606/98 |
| 4,535,768 | 8/1985 | Hourahane et al. | 606/96 |
| 4,668,233 | 5/1987 | Seedholm et al. | 623/13 |
| 4,672,957 | 6/1987 | Hourahane | 606/96 |
| 4,708,139 | 11/1987 | Dunbar | 606/96 |
| 4,739,751 | 4/1988 | Sapega | 606/96 |
| 4,823,780 | 4/1989 | Odensten et al. | 606/96 |
| 4,901,711 | 2/1990 | Goble et al. | 606/98 |
| 4,920,958 | 5/1990 | Walt et al. | 606/96 |
| 4,945,904 | 8/1990 | Bolton | 606/96 |
| 4,985,032 | 1/1991 | Goble | 606/96 |

FOREIGN PATENT DOCUMENTS 0126520 11/1984 European Pat. Off. .
2078528 1/1982 United Kingdom .

*Primary Examiner*—Michael A. Brown
*Attorney, Agent, or Firm*—M. Reid Russell

[57] ABSTRACT

A femoral tunnel entry drill guide for drilling a transverse hole from the side of a patient's knee to intersect a femoral section of a bony ligament tunnel formed in an arthroscopic surgical procedure. The drill guide of the invention has spaced apart parallel reference and external rods, an end of each connecting to ends of a web member forming a U-shaped device, the opposite rod ends bent at equal arcuate angles from the rod longitudinal axis. Each rod bent end has a transverse hole formed laterally therethrough, which holes align, and the external rod bent end transverse hole is threaded to receive a guide sleeve turned therethrough that has a straight bore for receiving a drill turned therethrough. Which reference rod bent end includes a longitudinal slot formed form the rod end to intersect the transverse. The reference rod bent end is fitted through a port formed through the skin of the knee, below the patella, and into the femoral tunnel section end in the intra articular joint. After entry, the drill guide reference rod is pivoted as the reference rod bent end slides into the femoral tunnel section, with a hole drilled through the external rod bent end transverse hole and into the distal femur to intersect the reference rod bent end transverse hole.

5 Claims, 2 Drawing Sheets

FEMORAL TUNNEL ENTRY DRILL GUIDE

BACKGROUND OF THE INVENTION

1. Field of the Invention

This invention relates to surgical devices and particularly to drill guiding devices that are used in arthroscopic surgical procedures in knee reconstructive surgery where a surgeon forms tibial and femoral tunnel sections that pass through the ligament points or origin, the tunnel sections for receiving a prosthetic or biologic ligament secured therein, replacing the anterior or posterior cruciate ligament.

2. Prior Art

The invention is for use in an anterior or posterior cruciate ligament repair and replacement surgical procedure where tibial and femoral tunnel sections are formed to pass through the ligament points of origin, the tunnel sections for maintaining a ligament therein spanning the intra articular joint. With the knee bent to approximately ninety (90) degrees, the tibial and femoral tunnel sections form approximately a straight tunnel, facilitating fitting a ligament end therein. To provide an interference mounting for maintaining a ligament end endosteally secured in a tunnel section, it is required to form a transverse passage that intersects the tunnel section. Accordingly, drill guides referencing the prepared aligned tibial and femoral tunnel sections to direct drilling an intersecting hole from without the knee to intersect a point along that tunnel have been developed. Meeting this need, the present invention is the inventor of two earlier U.S. Pat. Nos. 4,901,711 and 4,985,032, for drilling a transverse passage or hole from without the knee to intersect, at a right angle, a point along the aligned tunnel sections. Also, the present inventor is the inventor of an invention in a "Sight Barrel Arthroscopic Instrument", U.S. patent application No. 07/580,172, for forming a tunnel intersecting hole from within the knee to intersect, at an acute angle, a point along a tunnel section. Which earlier drill guides all reference the aligned tibial and femoral tunnel sections by fitting a straight reference rod therein. Whereas, the present invention utilizes a bent reference rod for arthroscopic insertion into the intra articular joint end of the femoral tunnel section.

The above set out drill guides are for forming passages or holes that intersect ligament mounting tunnels. Whereas, earlier drill guides for use in knee arthroscopic surgical procedures were for drilling, from without the knee, to a locator point positioned within the intra articular joint. Examples of such earlier devices are shown in patents to Walt, et al, U.S. Pat. No. 4,920,958; to Sapega, et al, U.S. Pat. No. 4,739,751; to Cho, U.S. Pat. No. 4,257,411; to Hourahane, et al, U.S. Pat. No. 4,535,768; to Hourahane, et al, U.S. Pat. No. 4,672,957; and a United Kingdom Patent to Lovell, et al, No. 2,078,528. Other earlier devices for drilling tibial and femoral tunnel sections are shown in patents to Odensten, et al, U.S. Pat. No. 4,823,780; to Seedholm, et al, U.S. Pat. No. 4,668,233; and a European Patent Application No. 126520. None of which patents involve a femoral entry drill guide intersecting hole as does the present invention.

SUMMARY OF THE INVENTION

It is a principal object of the present invention in a drill guide for use in a straight tunnel cruciate ligament replacement surgical procedure to provide for drilling, from one side of the knee intra articular joint, a hole intersecting a femoral tunnel.

Another object of the present invention is to provide a drill guide that incorporates a reference rod for femoral tunnel end entry through an arthroscopic port formed in the front of the knee.

Another object of the present invention is to provide a drill guide incorporating a bent reference rod for convenient fitting through the arthroscopic port formed in the front of the knee and into the femoral tunnel end, the reference rod, above the bend, having a lateral receiving hole formed therethrough that a drill or pin is directed to from the side of the knee.

Another object of the present invention is to provide a drill guide where the receiving hole through the reference rod bent end is intersected by a longitudinal slot formed from the rod end for allowing a pin fitted through the receiving port to slid therealong, the pin remaining in place, as the drill guide reference rod is pulled out from the femoral tunnel section.

Still another object of the present invention is to provide a drill guide that includes a guide sleeve, for fitting through an external rod of which drill guide, for directing a drill or pin therethrough and to the lateral receiving hole of the reference rod bent end.

Still another object of the present invention is to provide a drill guide that is simple in its construction and is easy to use for forming a hole through the side of the knee, above the intra articular joint to intersect, at a right angle, a point along a femoral tunnel section.

The femoral entry drill guide of the invention is for use in an arthroscopic surgical procedure for forming a right angle passage or hole from the side of the knee, above the intra articular joint, to intersect a point along a femoral tunnel section. The drill guide includes parallel reference and external rods connecting, at their lower ends, to the ends of a web member that may be a one hundred eighty (180) degree bend at a mid-point of a straight rod for forming the parallel reference and external rods.

The reference rod is bent at an arcuate angle from the longitudinal axis thereof, to accommodate fitting its end through a port that is formed arthroscopically into the knee intra articular joint, below the patella. The external rod is bent identically to the reference rod, and has a hole formed laterally therethrough that is threaded to accommodate a guide sleeve turned therethrough. The guide sleeve includes a threaded barrel and smooth barrel extension extending from one end thereof. The barrel and barrel extension have a center longitudinal bore formed therethrough that, when the guide sleeve is installed through the external rod threaded hole, exactly points to a lateral hole that is formed through the reference rod, above the bend. The guide sleeve is for guiding drilling or directing a pin fitted therethrough and through the side of the knee to intersect the reference rod bent end lateral hole. A longitudinal slot is formed from the reference rod end to the lateral hole that is for allowing a drill or pin fitted through which reference rod lateral hole to slide therealong as the drill guide reference rod is pulled from the femoral tunnel section.

THE DRAWINGS

These and other objects and features of the present invention in a femoral tunnel entry drill guide will become more fully apparent from the following description in which the invention is described in detail in conjunction with the accompanying drawings.

Figure 2:
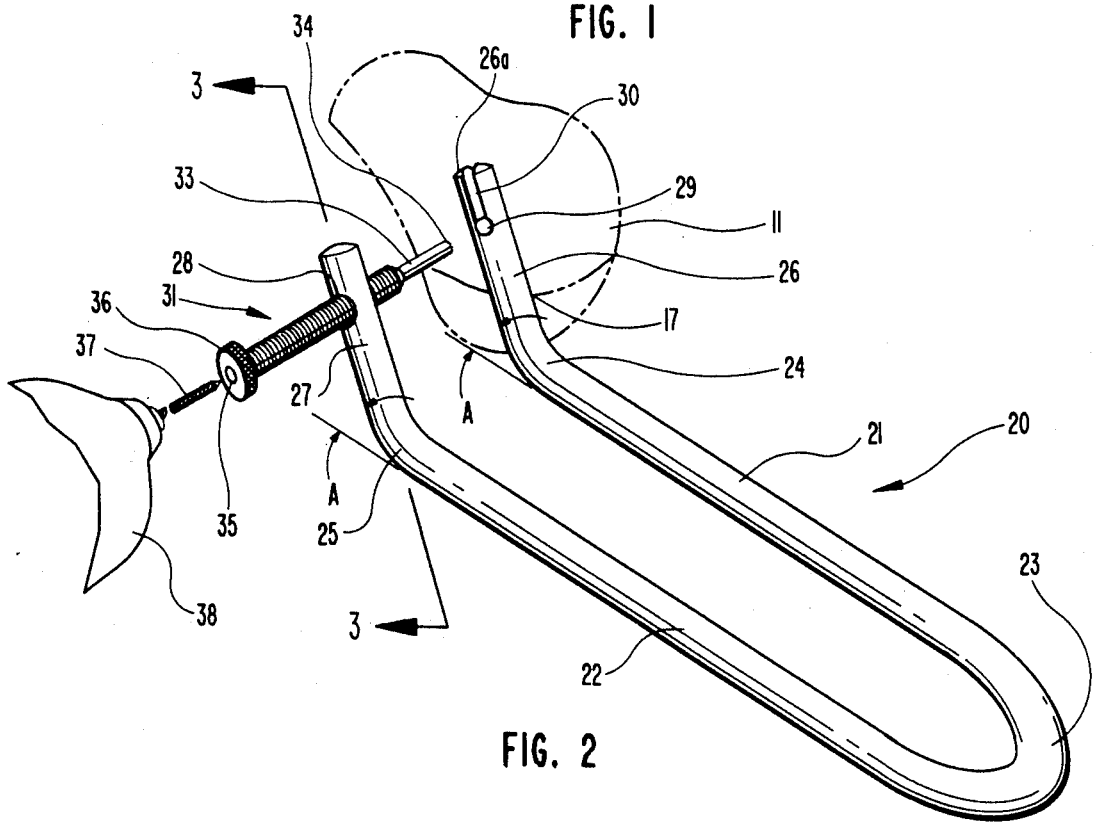
FIG. 2 shows the drill guide of FIG. 1 and the distal femur, shown in broken lines, removed from the knee, showing a threaded guide sleeve of the drill guide turned into a drill guide external rod threaded hole and showing a drill aligned for turning through which guide sleeve and into a lateral hole formed through the reference rod.
Figure 3:
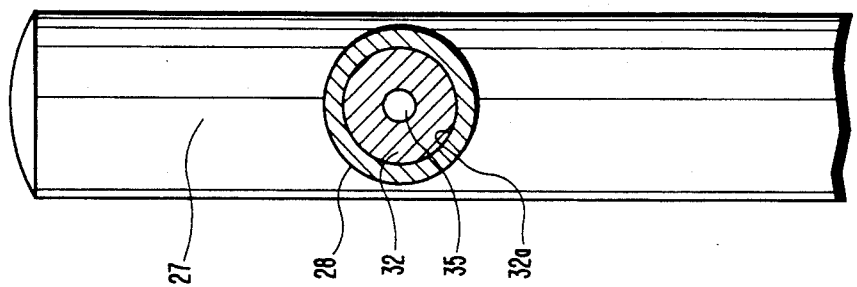
Figure 4:
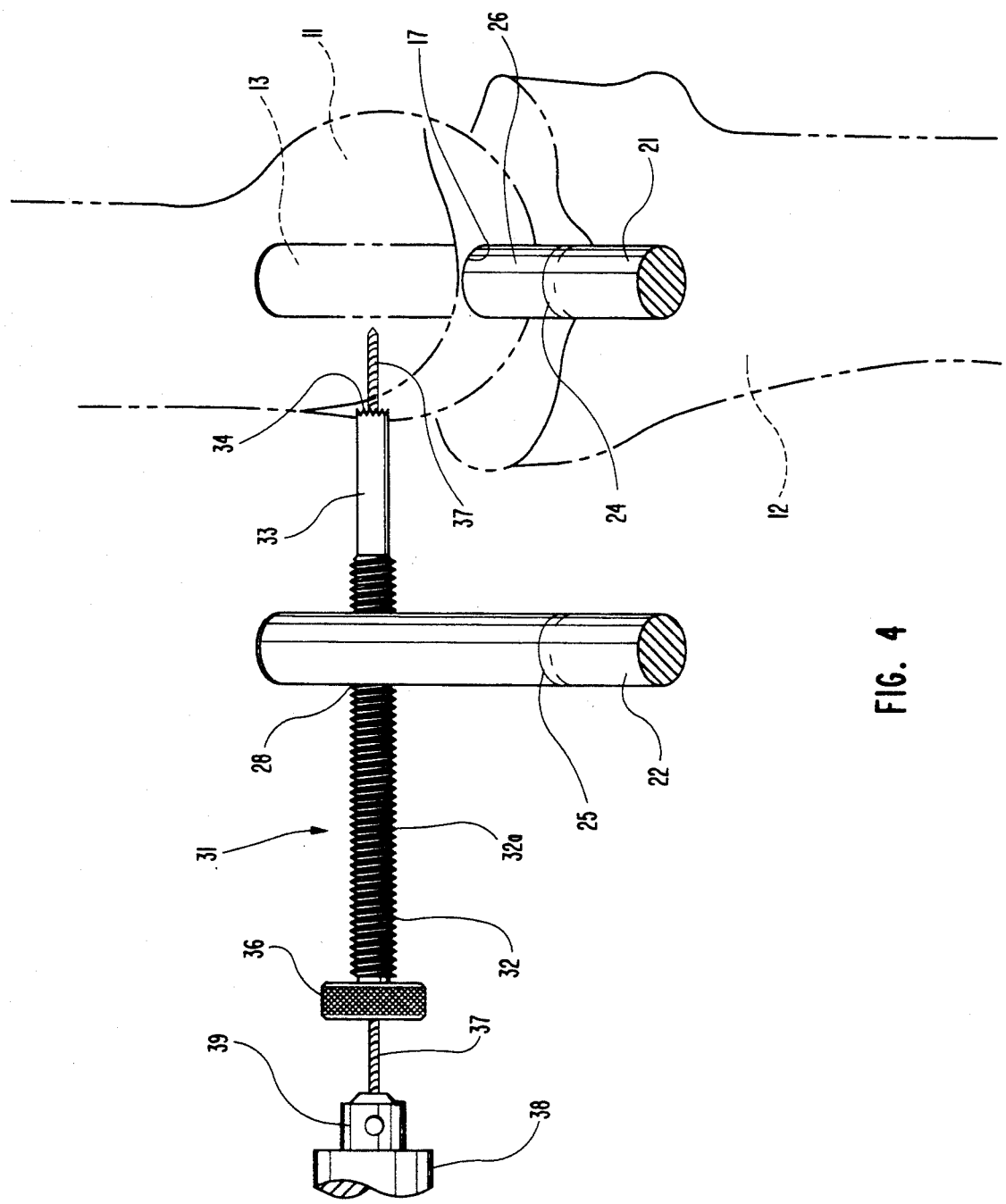

FIG. 3 shows a side elevation sectional view taken along the line 3—3 of FIG. 2; and FIG. 4 shows an enlarged front elevation view of the knee with the distal femur and proximal tibial shown in broken lines and the drill guide reference and external rods broken away below the bends and showing the guide sleeve turned through the external rod threaded hole and a drill turned through which guide sleeve to the reference rod bent end.

DETAILED DESCRIPTION

Figure 1:
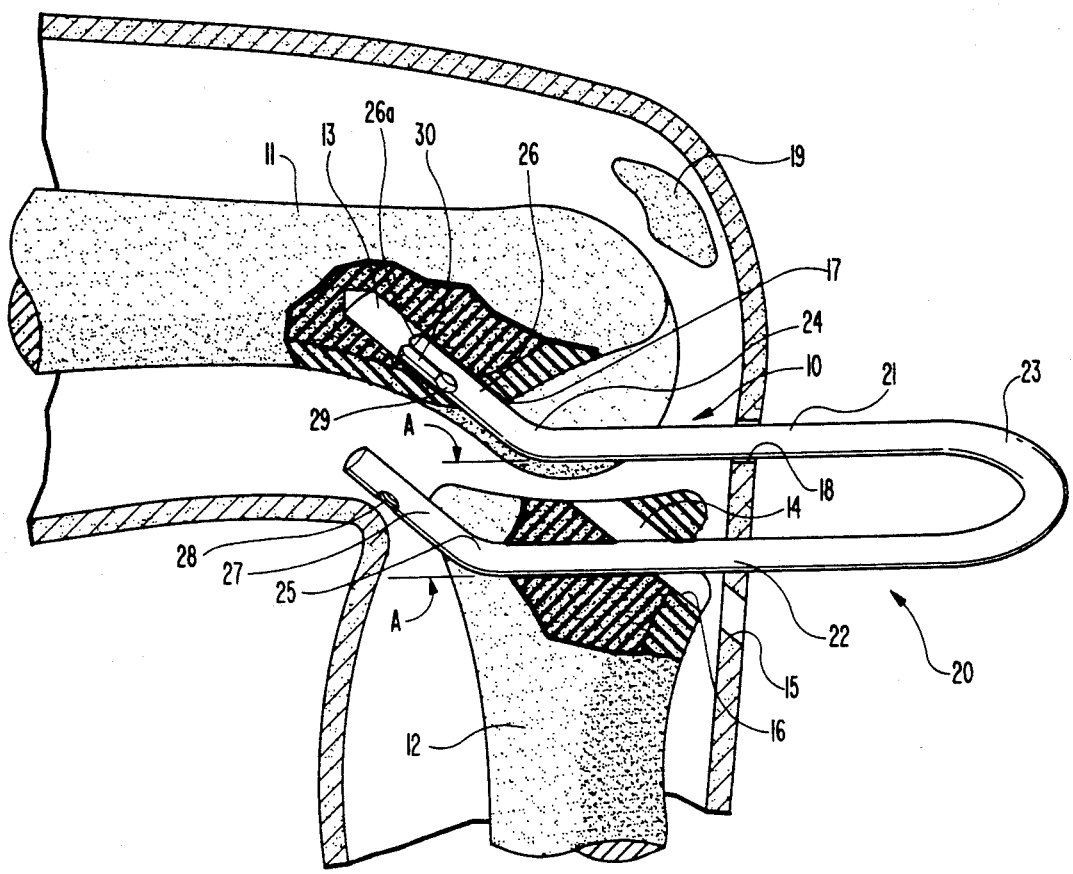
FIG. 1 is a side elevation view of a patient's knee showing the intra articular joint of the distal femur and proximal tibia, wherefrom a longitudinal section of covering skin has been removed, and a reference rod of a femoral tunnel entry drill guide of the invention installed in a femoral tunnel section of a straight ligament tunnel.

FIG. 1 shows a side elevation view of an intra articular knee joint 10, with the distal femur 11 and proximal tibia 12 shown bent to approximately a right angle. With the knee bent, a straight ligament tunnel, shown as femoral and tibial tunnel sections 13 and 14, respectively, is formed across the intra articular joint 10, passing through the ligament points of origin. Which straight ligament tunnel is for receiving a natural or prosthetic ligament mounted therein in ligament replacement procedure. The tibial tunnel section is formed through the skin of the knee at 15, and drilled through the anteromedial cortex of the proximal tibia at 16. The femoral tunnel section is drilled through the distal femur at approximately four (4) millimeters anterior to the juncture of the femur posterior cortex and the intercondylar seam, forming entry hole 17, with the femur tunnel section terminating in the femur endosteum. A second port 18 is formed through the knee skin into the intra articular joint, beneath the patella 19, providing access to the femoral tunnel section end 17.

A femoral tunnel entry drill guide 20 of the invention, hereinafter referred to as drill guide, is shown in FIG. 1 installed through the port 18 and entry hole 17 and is seated in the femoral tunnel section 13. The drill guide 20 is shown as having a U-shape with identical parallel reference and external rods 21 and 22, respectively, whose bottom ends are connected to ends of a web member 23 that is bent through one hundred eighty (180) degrees. The reference and external rods 21 and 22 are shown bent at 24 and 25 at identical arcuate angles from the longitudinal axis of which reference and external rods. The bends, as shown best in FIG. 2, are identified as angles A, with upper reference and external rod ends 26 and 27, respectively, shown extending from which bends. The angles A is approximately 30 degrees.

The reference rod 21 end 26 is for fitting into the femoral tunnel section 13, the arcuate bend 24 allowing the reference rod end 26 to be fitted, at approximately a right angle, through the skin port 18 and is then pivoted to fit through the femoral tunnel section end 17. Whereafter the reference rod end 26 is slid into which femoral tunnel section 13, as shown. So arranged, the external rod 22 extends alongside the left side of the knee, alongside the reference rod 21. So arranged, a threaded transverse hole 28 is formed laterally through which external rod end 27 exactly aligns with a transverse hole 29 formed laterally through the reference rod end 26. Which reference rod end 26 has a longitudinal slot 30 formed from the rod flat end 26a to intersect the transverse hole 29.

FIGS. 2 and 4 show the drill guide 20 of FIG. 1 as incorporating a guide sleeve 31 that consists of a threaded barrel section 32 with smooth barrel end 33 extending from one end thereof. Which smooth barrel end 33 includes, as shown best in FIG. 4, a serrated surface 34 across the end thereof, for engaging the knee surface. A straight bore 35 is formed through which threaded barrel and smooth barrel end for guiding a drill or pin turned therethrough. The threaded barrel 32 is for turning into the external rod 22 threaded transverse hole 28. Which turning is accomplished by manually turning a knob 36 that is secured across the threaded barrel end opposite to the smooth barrel end 33, and wherethrough the bore 35 is formed.

As set out above, the guide sleeve 31 bore 35 is for passing a drill or pin to intersect the transverse hole 29 formed through the reference rod 21 end 26. FIGS. 2 and 4 show a drill 37 being fitted into and turned therethrough and into the knee. Which drill 37 turning is provided by an electric drill 38, that mounts a chuck 39 wherein the drill 37 is maintained. FIG. 3 shows the arrangement of the guide sleeve 31 threaded body threads 32a turned through the threaded transverse hole 28 of the external rod 22 end 27 showing the open bore 35 wherethrough the drill 37 is turned.

In practice, with the drill guide 20 installed, as shown in FIGS. 1 and 2, including the guide sleeve 32 fitted thereto, a first hole is drilled through the patient's skin the into the distal femur 11 to intersect the femoral tunnel section 13. A pin, or the like, not shown can then be fitted into the hole formed by which drilled hole, the end positioned in the reference rod lateral hole 29. So arranged, the longitudinal slot 30 in the reference rod end 26 will allow the reference rod 21 to be removed from the femoral tunnel section 13, the pin sliding along the slot 30. Which reference rod 21 removal requires release of the drill or pin out from the external rod transverse threaded hole 28. A prosthetic or biologic ligament, not shown, can be fitted through the tibial tunnel section 14 and into the femoral tunnel section 13. In such ligament fitting, the pin is pulled just out of which femoral tunnel section, allowing the ligament end to pass thereby, and which pin is then refitted into the femoral tunnel section passing into the ligament end, securing it therein.

A preferred embodiment of the present invention in a femoral tunnel entry drill guide has been shown and described herein. It should, however, be apparent that this disclosure is made by way of example only, and that variations and modification to the drill guide and its use are possible within the scope of this disclosure without departing from the subject matter coming within the scope of the following claims and a reasonable equivalency thereof, which claims I regard as my invention.

I claim:

1. A femoral tunnel entry drill guide comprising, a reference rod and an external rod, each formed from a straight rod section, an end of each connected to an end of a web member, which said reference and external rods are parallel to one another and each is bent at its end opposite to the web member coupling ends at identical arcuate angles from each rod section longitudinal axis, and said reference and external rod bent ends each have a transverse hole formed therethrough, which holes are aligned; and guide means for mounting to the external rod bent end transverse hole for guiding drilling to the reference rod bent end transverse hole.

2. A femoral tunnel entry drill guide as recited in claim 1, wherein the external and reference rods and the web member are formed from a straight rod section that is bent upon itself.

3. A femoral tunnel entry drill guide as recited in claim 1, wherein the external and reference rod ends are bent at approximately thirty (30) degrees angles to the rods longitudinal axis, the and the reference rod end is slotted longitudinally from the end thereof to the transverse hole.

4. A femoral tunnel entry drill guide as recited in claim 1, wherein the external rod end transverse hole is threaded to receive, as the guide means, a threaded barrel portion of a guide sleeve that includes a straight bore therethrough for receiving a drill.

5. A femoral entry drill guide as recited in claim 4, wherein the guide sleeve includes a smooth barrel portion extending longitudinally from an end of the threaded barrel portion and includes serrations formed across its opposite end; and a knob means for manual turning formed across the threaded barrel portion end opposite to the smooth barrel portion end.

* * * * *